United States Patent [19]

Matsui et al.

[11] Patent Number: 4,871,674

[45] Date of Patent: Oct. 3, 1989

[54] CULTURE CELL

[75] Inventors: Shigeaki Matsui, Hirakata; Eiichi Hirai, Takarazuka; Junji Nakamura, Suita, all of Japan

[73] Assignee: Kurashiki Boseki Kabushiki Kaisha, Kurashiki, Japan

[21] Appl. No.: 255,565

[22] Filed: Oct. 11, 1988

[30] Foreign Application Priority Data

Oct. 12, 1987 [JP] Japan ............................ 62-156202[U]

[51] Int. Cl.$^4$ .......................... C12M 3/00; B01L 3/00
[52] U.S. Cl. ..................................... 435/284; 422/102; 435/240.25; 435/240.46; 435/285
[58] Field of Search ....................... 435/240.25, 240.46, 435/284, 285, 286, 311; 422/101, 102, 104; 210/337, 338, 339

[56] References Cited

U.S. PATENT DOCUMENTS

| 4,446,234 | 5/1984 | Russo et al. | 435/240.241 X |
| 4,608,342 | 8/1986 | Nees | 435/284 X |
| 4,748,124 | 5/1988 | Vogler | 435/285 X |

FOREIGN PATENT DOCUMENTS 62-155078  7/1987  Japan.
0239697 10/1987  Japan.

Primary Examiner—Barry S. Richman
Assistant Examiner—Jeffrey R. Snay
Attorney, Agent, or Firm—Armstrong, Nikaido Marmelstein Kubovcik & Murray

[57] ABSTRACT

A culture cell having discontinuous projecting parts for hanging the culture cell on an upper circumferential portion and a membrane filter on a bottom portion, characterized in that triangular tapered ribs are provided continuously underneath the discontinuous projecting parts.

1 Claim, 2 Drawing Sheets

PRIOR INVENTION

PRIOR INVENTION

CULTURE CELL

BACKGROUND OF THE INVENTION

The present invention relates to a culture cell which is used in combination with a culture plate.

Hitherto a culture device shown in a schematic typical cross-sectional view of FIG. 11 which comprises plural culture wells 4 arranged on a culture plate 5 and culture cells 6 having membrane filters 2 has been used for studies on intercellular interaction, metabolism of cells and the like for the reasons that the studies on intercellular interactions of different kinds of cells can be carried out not only without contacts thereof but also under an in vitro system which is closely akin to the in vivo system.

However, such a culture device has several disadvantages. For example, cells to be cultured are injured by legs 8 of the culture cell 6 because the culture cell 6 is not fixed, and therefore, good reproducibility is hard to obtain. Furthermore, excess cells to be cultured are adhered to the legs 8, and therefore, a uniform cultivation cannot be achieved.

More recently, a culture cell shown in a schematic corss-sectional view of FIG. 12 is commercially available as "Transwell" (Costar Co., United States of America, Massachusetts, Cambridge) in order to solve these disadvantages. The culture cell 6 has a projecting part 1 for hanging the culture cell which is provided over the whole upper circumferential part, openings 7 for exchanging gas and for pipetting sample which are bored in the sidewall and membrane filter 2 which is provided on the bottom.

However, this improved culture cell has several disadvantages. For example, the gases are not exchanged sufficiently because the area of the openings 7 is small. Futhermore, culture capacity is restricted and culture liquid in inside and outside portions of the culture cell is apt to contaminate because the openings 7 are provided in the sidewall of the culture cell.

The present inventors have previously offered a culture cell 6 shown in FIG. 13 and FIG. 14 which comprises discontinuous projecting parts 1 for hanging the culture cell 6 provided on an upper circumferential part and a membrane filter 2 provided on a bottom, said culture cell having none of the aforesaid problems (Japanese Utility Model Application No. 77503/1987).

Although it is possible to pipet sample through a space between the culture cell 6 and the culture well 4 and to pour a culture medium for an exchange and the like into the space through the openings 7 without detaching the culture cell 6 from culture plate 5, the culture cell has a problem in that the diameter of the culture cell must be diminished in order to insert the tip of a micropipet into the openings 7, and therefore, an inside capacity of the culture cell and an effective area of the membrane filter are reduced and efficiencies of operation, cultivation and the like are decreased.

The object of the present invention is to provide an improved culture cell having none of the aforementioned problems.

SUMMARY OF THE INVENTION

The present invention relates to a culture cell having discontinuous projecting parts for hanging the culture cell on an upper circumferential portion and a membrane filter on a bottom, characterized in that triangular tapered ribs are provided continuously underneath the discontinuous projecting parts.

DETAILED DESCRIPTION OF THE INVENTION

Although the numbers of the projecting parts 1 for hanging the culture cell depend on their shapes, sizes and the like and therefore are not restricted, too many projecting parts bring about more limited movable range of the culture cell within the culture well and are not preferred. The numbers are normally three (the angle between adjacent projecting parts is about 120°) or four (the angle between adjacent projecting parts is about 90°), especially three.

As the materials of the membrane filter 2 provided on the bottom of the culture cell 6, those hitherto used for such a culture cell, for example, mixed cellulose ester, polycarbonate, polyethylene terephthalate, polysulfone polytetrafluoroethylene, collagen and the like may be used.

The characteristic of the culture cell according to the present invention resides in the triangular tapered ribs 9 which are provided continuously underneath the discontinuous projecting parts. 1.

An angle between inclined planes of the ribs 9 and the sidewall of the culture cell is usually about 20–60°, especially 25°–45°.

Figure 8:
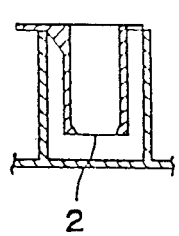
FIG. 8 is a cross-sectional view of the culture cell and well taken along with section line A—A in FIG. 7.

As shown in FIG. 8, while the edges of the inclined planes which extend toward radial direction of the ribs 9, i.e. toward the projecting parts, come into contact with the inside wall of the upper edges of the culture well in a usual hanging state as shown in FIG. 8 or are situated so as to form a narrow space between said inside wall and them, the edges of the inclined planes which extend along the outside wall of the culture cell do not exceed half of the height of the culture cell in general.

Figures 1, 3, 5:
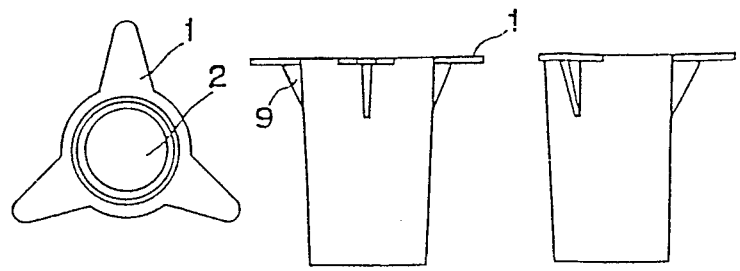
FIG. 1 is a plan view of one embodiment of the culture cell according to the present invention.
FIG. 3 is a back view of the culture cell shown in FIG. 1.
FIG. 5 is a right side view of the culture cell shown in FIG. 1.
Figures 2, 4, 6:
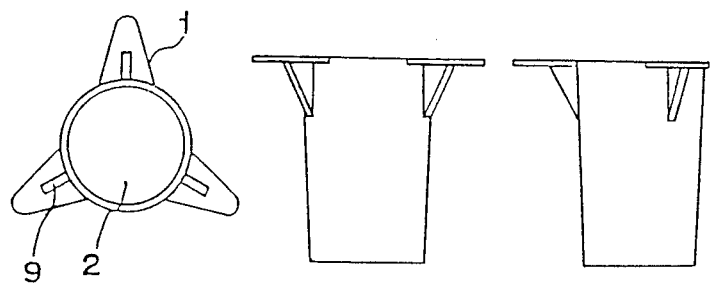
FIG. 2 is a base view of the culture cell shown in FIG. 1.
FIG. 4 is a front view of the culture cell shown in FIG. 1.
FIG. 6 is a left side view of the culture cell shown in FIG. 1.
Figures 7, 9:
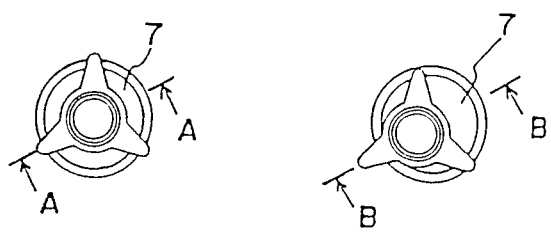
FIG. 7 is a plan view of the culture cell shown in FIG. 1-6 which is hung on the culture well.
FIG. 9 is a plan view of the culture cell which is shifted its hung position on the culture well shown in FIG. 7 and FIG. 8 to upward diagonal direction by inserting the tip of the micropipet (not shown) into the space between outside wall of the culture cell and inside wall of the culture well and pressing the culture cell against the inside wall of the culture well.
Figure 10:
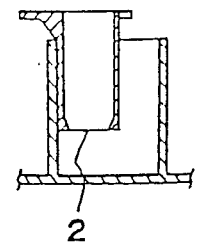
FIG. 10 is a cross-sectional view of the culture cell and well taken along with section line B—B in FIG. 9.
Figure 11:
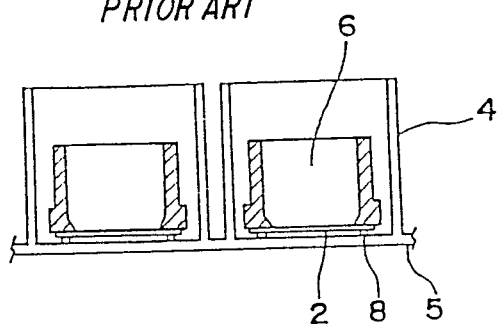
FIG. 11 is a cross-sectional view of the former culture device.
Figure 12:
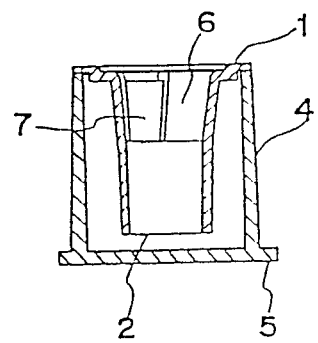
FIG. 12 is a cross-sectional view of the former improved culture device.
Figure 13:
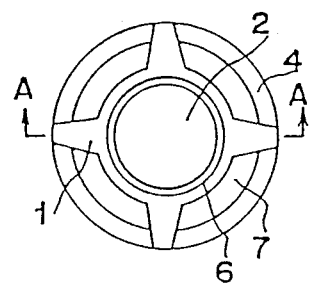
FIG. 13 is a plan view of the another former improved culture device hung on the culture well.
Figure 14:
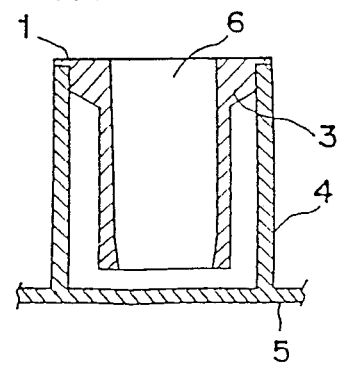
FIG. 14 is a cross-sectional view of the culture cell and well taken along with section line A—A in FIG. 13.

In the case where cultivation is carried out in the state shown in FIG. 7 and FIG. 8 and the sample in the space surrounded by the culture cell 6 and culture well 4 is withdrawn or the culture medium for an exchange and the like are poured into said space, the tip of the micropipet is inserted into the openings 7 and therefore the openings 7 are expanded as shown in FIG. 9 and FIG. 10 because the tapered ribs 9 are pushed up diagonally upward direction along the inclined planes of the tapered ribs 9. Accordingly, the withdrawal of the sample, the pour of the culture medium for an exchange and the like can be carried out safely and certainly by inserting the tip end of the micropipet into the bottom of the culture well 4.

When the tip of the micropipet is drawn out from the openings 7, an excess shearing force is not applied to the cell sample, culture medium and the like during the aforementioned operation because the culture cell 6 is slid smoothly in diagonally downward direction along the inclined planes of the tapered ribs 9 and returned to the stable hanging state as shown in FIG. 7 and FIG. 8.

Although the material of the body of the culture cell according to the present invention is not restricted particularly, said body is formed as one body from plastics such as polystyrene, polymethyl methacrylate, polyvinyl chloride, polymethylpentene, polycarbonate and the like because the culture cell is usually disposable.

According to the present invention, smooth insertion of devices for withdrawing and pouring the samples and the like such as tip of micropipet and the like into the space between the culture cell and well and smooth withdrawal of said devices from the space can be carried out safely and certainly without reducing the inside capacity of the culture cell and the effective area of the membrane filter.

What is claimed is:
1. A culture cell comprising;
   (a) a hollow chamber, having a top and a bottom, wherein the bottom of said chamber is formed by the attachment of a membrane filter,
   (b) a plurality of discontinuous projections extending radially outward from the top of said chamber beyond a sidewall of the chamber,
   (c) each said projection having attached to the bottom of the projection in an outwardly radially extending right triangular rib, each said rib being attached at the radially innermost end thereof to said chamber, each said rib being further oriented such that the right angled corner of said right triangular rib abuts the point of contact of said projection with said chamber.

* * * * *